US006486182B1

(12) United States Patent
Chang et al.

(10) Patent No.: US 6,486,182 B1
(45) Date of Patent: Nov. 26, 2002

(54) MUTUAL PRODRUGS OF AMLODIPINE AND ATORVASTATIN

(75) Inventors: George Chang, Ivoryton, CT (US); Ernest S. Hamanaka, Gales Ferry, CT (US); John L. LaMattina, Ledyard, CT (US)

(73) Assignee: Pfizer Inc, New York, NY (US)

( * ) Notice: Subject to any disclaimer, the term of this patent is extended or adjusted under 35 U.S.C. 154(b) by 0 days.

(21) Appl. No.: 09/577,561

(22) Filed: May 24, 2000

Related U.S. Application Data

(60) Provisional application No. 60/136,608, filed on May 27, 1999.

(51) Int. Cl.[7] ................. A61K 31/4439; C07D 401/12; C07D 405/14
(52) U.S. Cl. ..................................... 514/343; 546/276.4
(58) Field of Search ........................ 546/276.4; 514/343

(56) References Cited

U.S. PATENT DOCUMENTS

| | | | |
|---|---|---|---|
| 4,572,909 A | 2/1986 | Campbell et al. | 514/356 |
| 4,681,893 A | 7/1987 | Roth | 514/422 |
| 4,879,303 A | 11/1989 | Davison et al. | 514/356 |
| 5,155,120 A | 10/1992 | Lazar et al. | 514/356 |
| 5,273,995 A | 12/1993 | Roth | 514/422 |

FOREIGN PATENT DOCUMENTS

| | | | |
|---|---|---|---|
| WO | WO9911259 | 3/1999 | A61K/31/44 |

OTHER PUBLICATIONS

The Merck Index, Twelfth Edition, pp. 86, 87 & 146, Pub. by Merck & Co.,Inc. 1996.*
Hans Bundgaard, "Design of Prodrugs", pp. 3–10, Published by Elsevier 1985.*
Orekhov et al., Cardiovascular Drugs and Therapy, 1997, 11, 350.
Jukema et al., Circulation, 1995, Suppl. 1, I–197.
Lichtlen, P.R. et al., Lancet, 1990, 335, 1109–13.
Waters, D. et al., Circulation, 1990, 82, 1940–53.
Wilson et al., Am. J. Cardiol. 1987, 59(14), 91G–94G.
Kramsch et al., Jorunal of Human Hypertension, 1995, Suppl. 1, S3–S9.
Brown and Goldstein, New England Journal of Medicine, 1981, 305, No. 9, 515–517.
The Scandinavian Simvastatin Survival Study Group, Lancet, 1994, 344, 1383–89.
Shepherd J. et al., New England Journal of Medicine, 1995, 333, 1301–07.
A. Vigroux, Bergon, M. Bioorg. Med. Chem. Lett, 1995, 427–430.
G.R. Brown et al., Bioorg. Med. Chem. Lett, 1996, 6, 273–278.

* cited by examiner

*Primary Examiner*—Charanjit S. Aulakh
(74) *Attorney, Agent, or Firm*—Peter C. Richardson; Gregg C. Benson; Robert T. Ronau

(57) ABSTRACT

This invention relates to mutual prodrugs of amlodipine and atorvastatin and to pharmaceutical compositions thereof. This invention also relates to methods of treating angina pectoris, atherosclerosis, and hypertension and hyperlipidemia in a mammal using those prodrugs and compositions. This invention also relates to methods of managing cardiac risk in a mammal, including humans, presenting with symptoms of cardiac risk by administering those prodrugs and compositions.

47 Claims, No Drawings

MUTUAL PRODRUGS OF AMLODIPINE AND ATORVASTATIN

This application is filed claiming priority from co-pending Provisional Application No. 60/136,608 filed May 27, 1999.

This invention relates to mutual prodrugs of amlodipine and atorvastatin, pharmaceutically acceptable acid addition salts thereof, pharmaceutical compositions thereof and methods of using such prodrugs and compositions to treat subjects suffering from angina pectoris, atherosclerosis, combined hypertension and hyperlipidemia and to treat subjects presenting with symptoms of cardiac risk, including humans.

BACKGROUND OF THE INVENTION

The conversion of 3-hydroxy-3-methylglutaryl-coenzyme A (HMG-CoA) to mevalonate is an early and rate-limiting step in the cholesterol biosynthetic pathway. This step is catalyzed by the enzyme HMG-CoA reductase. Statins inhibit HMG-CoA reductase from catalyzing this conversion. As such, statins are collectively potent lipid lowering agents.

Atorvastatin calcium, disclosed in U.S. Pat. No. 5,273,995, which is incorporated herein by reference, is currently sold as Lipitor® and has the formula

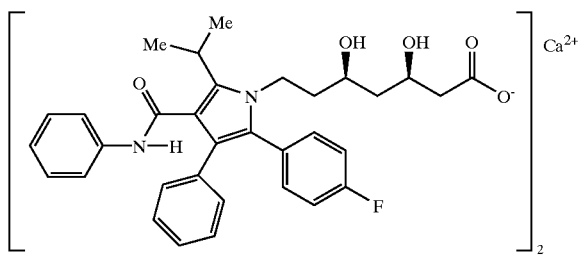

Atorvastatin calcium is a selective, competitive inhibitor of HMG-CoA. As such, atorvastatin calcium is a potent lipid lowering compound. The free carboxylic acid form of atorvastatin exists predominantly as the lactone of the formula

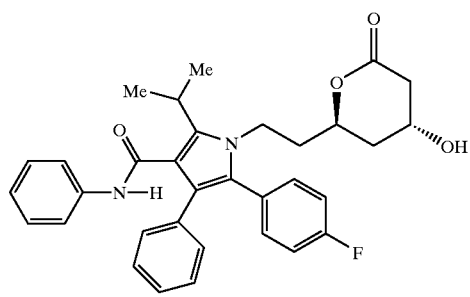

and is disclosed in U.S. Pat. No. 4,681,893, which is incorporated herein by reference.

Amlodipine and related dihydropyridine compounds are disclosed in commonly assigned U.S. Pat. No. 4,572,909, which is incorporated herein by reference, as potent anti-ischemic and antihypertensive agents. Commonly assigned U.S. Pat. No. 4,879,303, which is incorporated herein by reference, discloses amlodipine benzenesulfonate salt (also termed amlodipine besylate). Amlodipine and amlodipine besylate are potent and long lasting calcium channel blockers. As such, amlodipine, amlodipine besylate and other pharmaceutically acceptable acid addition salts of amlodipine have utility as antihypertensive agents and as antiischemic agents. Amlodipine and its pharmaceutically acceptable acid addition salts are also disclosed in commonly assigned U.S. Pat. No. 5,155,120 as having utility in the treatment of congestive heart failure. Amlodipine besylate is currently sold as Norvasc®. Amlodipine has the formula

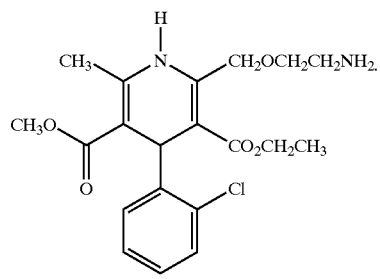

Atherosclerosis is a condition characterized by irregularly distributed lipid deposits in the intima of arteries, including coronary, carotid and peripheral arteries. Atherosclerotic coronary heart disease (hereinafter termed "CHD") accounts for about 53% of all deaths attributable to a cardiovascular event. CHD accounts for nearly one-half (about $50–60 billion) of the total U.S. cardiovascular healthcare expenditures and about 6% of the overall national medical bill each year. Despite attempts to modify secondary risk factors such as, inter alia, smoking, obesity and lack of exercise, and treatment of dyslipidemia with dietary modification and drug therapy, CHD remains the most common cause of death in the United States.

High levels of blood cholesterol and blood lipids are conditions involved in the onset of atherosclerosis. It is well known that inhibitors of 3-hydroxy-3-methylglutaryl-coenzyme A reductase (HMG-COA reductase) are effective in lowering the level of blood plasma cholesterol, especially low density lipoprotein cholesterol (LDL-C), in man (Brown and Goldstein, New England Journal of Medicine, 1981, 305, No. 9, 515–517). It has now been established that lowering LDL-C levels affords protection from coronary heart disease (see, e.g., The Scandinavian Simvastatin Survival Study Group: Randomised trial of cholesterol lowering in 4444 patients with coronary heart disease: the Scandinavian Simvastatin Survival Study (4S), Lancet, 1994, 344, 1383–89; and Shepherd, J. et al., Prevention of coronary heart disease with pravastatin in men with hypercholesterolemia, New England Journal of Medicine, 1995, 333, 1301–07).

Angina pectoris is a severe constricting pain in the chest, often radiating from the precordium to the left shoulder and down the left arm. Often angina pectoris is due to ischemia of the heart and is usually caused by coronary disease.

Currently the treatment of symptomatic angina pectoris varies significantly from country to country. In the U.S., patients who present with symptomatic, stable angina pectoris are frequently treated with surgical procedures or PTCA. Patients who undergo PTCA or other surgical procedures designed to treat angina pectoris frequently experience complications such as restenosis. This restenosis may be manifested either as a short term proliferative response to angioplasty-induced trauma or as long term progression of the atherosclerotic process in both graft vessels and angioplastied segments.

The symptomatic management of angina pectoris involves the use of a number of drugs, frequently as a combination of two or more of the following classes: beta blockers, nitrates and calcium channel blockers. Most, if not all, of these patients require therapy with a lipid lowering agent as well. The National Cholesterol Education Program (NCEP) recognizes patients with existing coronary artery disease as a special class requiring aggressive management of raised LDL-C.

Amlodipine helps to prevent myocardial ischemia in patients with exertional angina pectoris by reducing Total Peripheral Resistance, or afterload, which reduces the rate pressure product and thus myocardial oxygen demand at any particular level of exercise. In patients with vasospastic angina pectoris, amlodipine has been demonstrated to block constriction and thus restore myocardial oxygen supply. Further, amlodipine has been shown to increase myocardial oxygen supply by dilating the coronary arteries.

Hypertension frequently coexists with hyperlipidemia and both are considered to be major risk factors for developing cardiac disease ultimately resulting in adverse cardiac events. This clustering of risk factors is potentially due to a common mechanism. Further, patient compliance with the management of hypertension is generally better than patient compliance with hyperlipidemia. It would therefore be advantageous for patients to have a single therapy which treats both of these conditions.

Coronary heart disease is a multifactorial disease in which the incidence and severity are affected by the lipid profile, the presence of diabetes and the sex of the subject. Incidence is also affected by smoking and left ventricular hypertrophy which is secondary to hypertension. To meaningfully reduce the risk of coronary heart disease, it is important to manage the entire risk spectrum. For example, hypertension intervention trials have failed to demonstrate full normalization in cardiovascular mortality due to coronary heart disease. Treatment with cholesterol synthesis inhibitors in patients with and without coronary artery disease reduces the risk of cardiovascular morbidity and mortality.

The Framingham Heart Study, an ongoing prospective study of adult men and women, has shown that certain risk factors can be used to predict the development of coronary heart disease. (see Wilson et al., Am. J. Cardiol. 1987, 59(14):91G–94G). These factors include age, gender, total cholesterol level, high density lipoprotein (HDL) level, systolic blood pressure, cigarette smoking, glucose intolerance and cardiac enlargement (left ventricular hypertrophy on electrocardiogram, echocardiogram or enlarged heart on chest X-ray). Calculators and computers can easily be programmed using a multivariate logistic function that allows calculation of the conditional probability of cardiovascular events. These determinations, based on experience with 5,209 men and women participating in the Framingham study, estimate coronary artery disease risk over variable periods of follow-up. Modeled incidence rates range from less than 1% to greater than 80% over an arbitrarily selected six year interval. However, these rates are typically less than 10% and rarely exceed 45% in men and 25% in women.

Kramsch et al., Journal of Human Hypertension (1995) (Suppl. 1), 53–59 disclose the use of calcium channel blockers, including amlodipine, to treat atherosclerosis. That reference further suggests that atherosclerosis can be treated with a combination of amlodipine and a lipid lowering agent. Human trials have shown that calcium channel blockers have beneficial effects in the treatment of early atherosclerotic lesions. (see, e.g., Lichtlen, P. R. et al., Retardation of angiographic progression of coronary artery disease by nifedipine, Lancet, 1990, 335, 1109–13; and Waters, D. et al., A controlled clinical trial to assess the effect of a calcium channel blocker on the progression of coronary atherosclerosis, Circulation, 1990, 82, 1940–53.) U.S. Pat. No. 4,681,893 discloses that certain statins, including atorvastatin, are hypolipidemic agents and as such are useful in treating atherosclerosis. Jukema et al., Circulation, 1995 (Suppl. 1), 1–197, disclose that there is evidence that calcium channel blockers act synergistically in combination with lipid lowering agents (e.g., HMG-CoA reductase inhibitors), specifically pravastatin. Orekhov et al., Cardiovascular Drugs and Therapy, 1997, 11, 350 disclose the use of amlodipine in combination with lovastatin for the treatment of atherosclerosis.

Commonly assigned International Patent Application Publication Number WO99/11259 discloses a combination of amlodipine and atorvastatin.

SUMMARY OF THE INVENTION

This invention is directed to compounds which are mutual prodrugs of amlodipine and atorvastatin and pharmaceutically acceptable salts thereof.

This invention is particularly directed to a mutual prodrug of amlodipine and atorvastatin having the formula I,

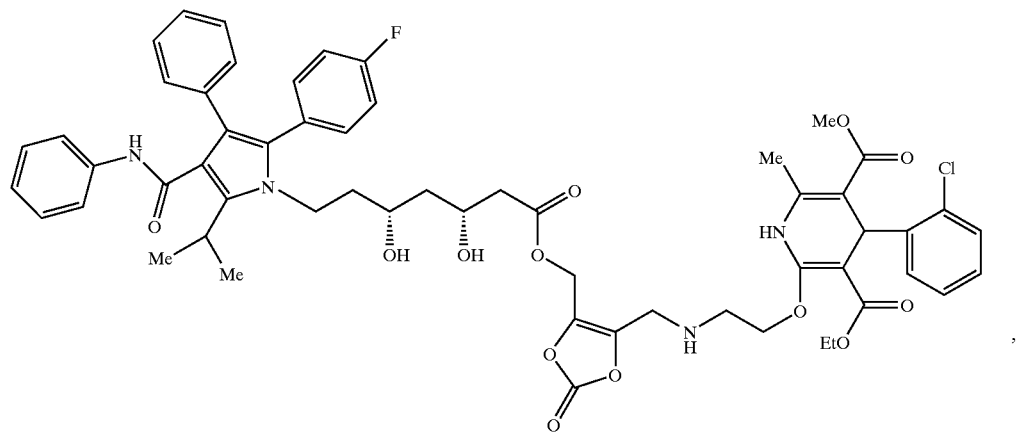

and pharmaceutically acceptable salts thereof.

This invention is more particularly directed to a compound of formula I wherein the carbon atom at the 4-position of the dihydropyridine ring has the (R)-configuration and pharmaceutically acceptable salts thereof.

This invention is also more particularly directed to a compound of formula I wherein the carbon atom at the 4-position of the dihydropyridine ring has the (S)-configuration and pharmaceutically acceptable salts thereof.

This invention is also directed to a mutual prodrug of amlodipine and atorvastatin which is a compound having the formula II,

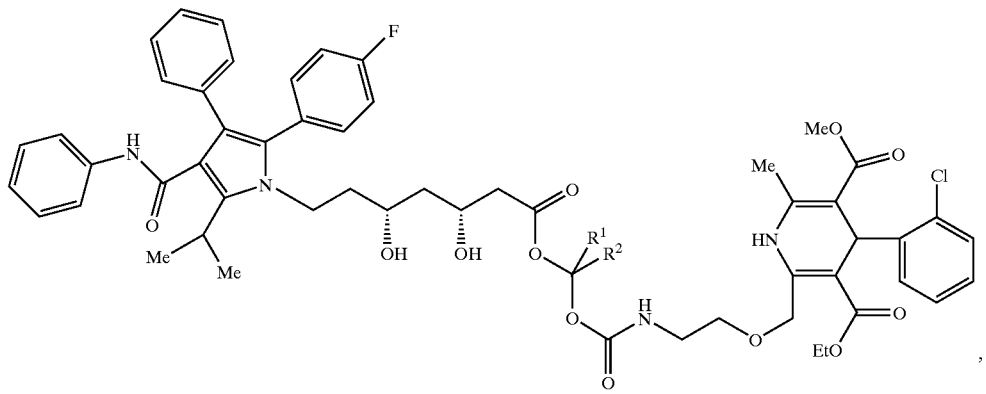

II wherein $R^1$ and $R^2$ are independently selected from H and $(C_1-C_4)$alkyl. It is particularly preferred that $R^1$ and $R^2$ are each H and pharmaceutically acceptable salts thereof.

This invention is more particularly directed to a compound of formula II wherein the carbon atom at the 4-position of the dihydropyridine ring has the (R)-configuration and pharmaceutically acceptable salts thereof.

This invention is also more particularly directed to a compound of formula II wherein the carbon atom at the 4-position of the dihydropyridine ring has the (S)-configuration and pharmaceutically acceptable salts thereof.

This invention is also directed to 4-(2-chloro-phenyl)-2-(2-[(5-{7-[2-(4-fluoro-phenyl)-5-isopropyl-3-phenyl-4-phenylcarbamoyl-pyrrol-1-yl]-3,5-dihydroxyheptanoyloxymethyl}-2-oxo-[1,3]dioxol-4-ylmethyl)-amino]-ethoxymethyl}-6-methyl-1,4-dihydro-pyridine-3,5-dicarboxylic acid 3-ethylester 5-methyl ester.

This invention is also directed to 4-(2-chloro-phenyl)-2-(2-{7-[2-(4-fluorophenyl)-5-isopropyl-3-phenyl-4-phenylcarbamoyl-pyrrol-1-yl]-3,5-dihydroxyheptanoyloxymethoxycarbonylamino}-ethoxymethyl)-6-methyl-1,4-dihydro-pyridine-3,5-dicarboxylic acid 3-ethyl ester 5-methyl ester.

This invention is also directed to pharmaceutical compositions comprising a mutual prodrug of amlodipine and atorvastatin or a pharmaceutically acceptable salt thereof and a pharmaceutically acceptable carrier, vehicle or diluent. This invention is particularly directed to such a composition wherein the prodrug is 4-(2-chloro-phenyl)-2-(2-[(5-{7-[2-(4-fluoro-phenyl)-5-isopropyl-3-phenyl-4-phenylcarbamoyl-pyrrol-1-yl]-3,5-dihydroxy-heptanoyloxymethyl}-2-oxo-[1,3]dioxol-4-ylmethyl)-amino]-ethoxymethyl}-6-methyl-1,4-dihydro-pyridine-3,5-dicarboxylic acid 3-ethylester 5-methyl ester or is 4-(2-chloro-phenyl)-2-(2-{7-[2-(4-fluoro-phenyl)-5-isopropyl-3-phenyl-4-phenylcarbamoyl-pyrrol-1-yl]-3,5-dihydroxy-heptanoyloxymethoxycarbonylamino}-ethoxymethyl)-6-methyl-1,4-dihydro-pyridine-3,5-dicarboxylic acid 3-ethyl ester 5-methyl ester.

This invention is also directed to methods of treating angina pectoris in a mammal suffering from angina pectoris comprising administering to said mammal an angina pectoris treating effective amount of a mutual prodrug of amlodipine and atorvastatin or a pharmaceutically acceptable salt thereof.

This invention is also directed to methods of treating angina pectoris in a mammal suffering from angina pectoris comprising administering to said mammal an angina pectoris treating effective amount of a pharmaceutical composition comprising a mutual prodrug of amlodipine and atorvastatin or a pharmaceutically acceptable salt thereof and a pharmaceutically acceptable carrier, vehicle or diluent.

This invention is also directed to methods of treating hypertension and hyperlipidemia in a mammal suffering from hypertension and hyperlipidemia comprising administering to said mammal a hypertension and hyperlipidemia treating effective amount of a mutual prodrug of amlodipine and atorvastatin or a pharmaceutically acceptable salt thereof.

This invention is also directed to methods of treating hypertension and hyperlipidemia in a mammal suffering from hypertension and hyperlipidemia comprising administering to said mammal a hypertension and hyperlipidemia treating effective amount of a pharmaceutical composition comprising a mutual prodrug of amlodipine and atorvastatin or a pharmaceutically acceptable salt thereof and a pharmaceutically acceptable carrier, vehicle or diluent.

This invention is also directed to methods of treating atherosclerosis in a mammal suffering from atherosclerosis comprising administering to said mammal an antiatherosclerosis effective amount of a mutual prodrug of amlodipine and atorvastatin or a pharmaceutically acceptable salt thereof. This invention is particularly directed to those cases where said antiatherosclerotic effect is manifested by a slowing of the progression of atherosclerotic plaques, including wherein said atherosclerotic plaque formation is slowed in coronary arteries, carotid arteries or in the peripheral arterial system. This invention is also particularly directed to those cases where said antiatherosclerotic effect is manifested by a regression of atherosclerotic plaques, including wherein said regression occurs in the coronary arteries, in the carotid arteries and/or in the peripheral arterial system.

This invention is also directed to methods of treating atherosclerosis in a mammal suffering from atherosclerosis comprising administering to said mammal an antiatherosclerosis effective amount of a pharmaceutical composition comprising a mutual prodrug of amlodipine and atorvastatin or a pharmaceutically acceptable salt thereof and a pharmaceutically acceptable carrier, vehicle or diluent.

This invention is also directed to methods of managing cardiac risk in a mammal at risk of suffering an adverse cardiac event, comprising administering to said mammal a cardiac risk treating effective amount of a mutual prodrug of amlodipine and atorvastatin or a pharmaceutically acceptable salt thereof.

This invention is also directed to methods of managing cardiac risk in a mammal at risk of suffering an adverse cardiac event, comprising administering to said mammal a cardiac risk treating effective amount of a pharmaceutical composition comprising a mutual prodrug of amlodipine and atorvastatin or a pharmaceutically acceptable salt thereof and a pharmaceutically acceptable carrier, vehicle or diluent.

This invention is also directed to methods of preparing atorvastatin in vivo by administering to a mammal, e.g., a human, a mutual prodrug of amlodipine and atorvastatin of this invention or a pharmaceutically acceptable salt thereof.

This invention is also directed to methods of preparing amlodipine in vivo by administering to a mammal, e.g., a human, a mutual prodrug of amlodipine and atorvastatin of this invention or a pharmaceutically acceptable salt thereof.

This invention is also directed to methods of treating a mammal with amlodipine comprising administering to said mammal a mutual prodrug of amlodipine and atorvastatin of this invention or a pharmaceutically acceptable salt thereof.

This invention is also directed to methods of treating a mammal with atorvastatin comprising administering to said mammal a mutual prodrug of amlodipine and atorvastatin of this invention or a pharmaceutically acceptable salt thereof.

This invention is also directed to pharmaceutical compositions comprising an amount of a mutual prodrug of amlodipine and atorvastatin of this invention or a pharmaceutically acceptable salt thereof and an amount of amlodipine or a pharmaceutically acceptable salt thereof, e.g., amlodipine besylate.

This invention is also directed to pharmaceutical compositions comprising an amount of a mutual prodrug of amlodipine and atorvastatin of this invention or a pharmaceutically acceptable salt thereof and an amount of atorvastatin or a pharmaceutically acceptable salt thereof, e.g., the hemicalcium salt of atorvastatin.

This invention is also directed to methods of treating angina pectoris in a mammal comprising administering to said mammal an amount of a mutual prodrug of amlodipine and atorvastatin or a pharmaceutically acceptable salt thereof and an amount of amlodipine or a pharmaceutically acceptable salt thereof, e.g., amlodipine besylate.

This invention is also directed to methods of treating atherosclerosis in a mammal comprising administering to said mammal an amount of a mutual prodrug of amlodipine and atorvastatin or a pharmaceutically acceptable salt thereof and an amount of amlodipine or a pharmaceutically acceptable salt thereof, e.g., amlodipine besylate.

This invention is also directed to methods of managing cardiac risk in a mammal comprising administering to said mammal an amount of a mutual prodrug of amlodipine and atorvastatin or a pharmaceutically acceptable salt thereof and an amount of amlodipine or a pharmaceutically acceptable salt thereof, e.g., amlodipine besylate.

This invention is also directed to methods of treating hypertension and hyperlipidemia in a mammal suffering from hypertension and hyperlipidemia comprising administering to said mammal an amount of a mutual prodrug of amlodipine and atorvastatin or pharmaceutically acceptable salt thereof and an amount of amlodipine or a pharmaceutically acceptable salt thereof, e.g., amlodipine besylate.

This invention is also directed to methods of treating angina pectoris in a mammal comprising administering to said mammal an amount of a mutual prodrug of amlodipine and atorvastatin or a pharmaceutically acceptable salt thereof and an amount of atorvastatin or a pharmaceutically acceptable salt thereof, e.g., the hemicalcium salt of atorvastatin.

This invention is also directed to methods of treating atherosclerosis in a mammal comprising administering to said mammal an amount of a mutual prodrug of amlodipine and atorvastatin or a pharmaceutically acceptable salt thereof and an amount of atorvastatin or a pharmaceutically acceptable salt thereof, e.g., the hemicalcium salt of atorvastatin.

This invention is also directed to methods of managing cardiac risk in a mammal comprising administering to said mammal an amount of a mutual prodrug of amlodipine and atorvastatin or a pharmaceutically acceptable salt thereof and an amount of atorvastatin or a pharmaceutically acceptable salt thereof, e.g., the hemicalcium salt of atorvastatin.

This invention is also directed to methods of treating hypertension and hyperlipidemia in a mammal suffering from hypertension and hyperlipidemia comprising administering to said mammal an amount of a mutual prodrug of amlodipine and atorvastatin or pharmaceutically acceptable salt thereof and an amount of atorvastatin or a pharmaceutically acceptable salt thereof, e.g., the hemicalcium salt of atorvastatin.

This invention is also directed to methods of treating a mammal comprising administering to said mammal an amount of a mutual prodrug of amlodipine and atorvastatin or a pharmaceutically acceptable salt thereof and an amount of atorvastatin or a pharmaceutically acceptable salt thereof, e.g., the hemicalcium salt of atorvastatin.

Amlodipine is a racemic compound due to the chiral carbon atom at position 4 of the dihydropyridine ring. The R and S enantiomers may be prepared as described by Arrowsmith et al., J. Med. Chem., 1986, 29, 1696. The calcium channel blocking activity of amlodipine is substantially confined to the S(−) isomer and to the racemic mixture containing the R(+) and S(−) forms. (see International Patent Application No. PCT/EP94/02697). The R(+) isomer has little or no calcium channel blocking activity. However, the R(+) isomer is a potent inhibitor of smooth muscle cell migration. Thus, the R(+) isomer is useful in the treatment or prevention of atherosclerosis. (see International Patent Application No. PCT/EP95/00847). Based on the above, a skilled person could choose to prepare an isomer of the compounds of this invention wherein the amlodipine portion is the R(+) isomer, the S(−) isomer or the racemic mixture of the R(+) isomer and the S(−) isomer.

Where used herein and in the appendant claims, the term "cardiac risk" means the likelihood that a subject will suffer a future adverse cardiac event such as, e.g., myocardial infarction, cardiac arrest, cardiac failure or cardiac ischaemia. Cardiac risk is calculated using the Framingham Risk Equation as set forth above. The term "cardiac risk management" means that the risk of future adverse cardiac events is substantially reduced.

DETAILED DESCRIPTION OF THE INVENTION

The mutual prodrugs of this invention may be readily prepared as set forth in the following description and in the Examples below. Specifically, to prepare the mutual prodrug of amlodipine and atorvastatin having the structure of formula I, atorvastatin is reacted with a 1,3-dioxolone derivative, preferably 4,5-bis(bromomethyl)-1,3-dioxol-2-one, in a reaction inert solvent in the presence of a suitable base and optionally a catalyst such as sodium iodide. As used herein, the expressions "reaction inert solvent" and "inert solvents" refer to a solvent or mixture of solvents which does not interact with starting materials, reagents, intermediates or products in a manner which adversely affects the yield of the desired product. A particularly preferred such solvent is ethyl acetate. Suitable bases for this reaction include inorganic bases such as potassium and sodium carbonate. The reaction is conducted at 0° C. to about ambient temperature for about four hours to about 16 hours. It is preferred to conduct the reaction at room temperature for about eight hours. The intermediate 2-oxo-1,3-dioxolane derivative of atorvastatin is isolated and reacted with amlodipine and a suitable base in a reaction inert solvent. A suitable such solvent is N,N-dimethylformamide. The reaction is conducted at 0° C. to about ambient temperature for about four hours to about 16 hours. It is preferred to conduct this reaction at 0° C. for about eight hours.

To prepare the mutual prodrug of amlodipine and atorvastatin having the structure of formula II, amlodipine is reacted with a chloromethyl chloroformate and a suitable organic base in a reaction inert solvent at a temperature of from −10° C. to about room temperature. This reaction is preferably conducted at 0° C. in chloroform. The preferred base for this reaction is pyridine. The reaction mixture is generally warmed to about ambient temperature to effect reaction. Usually the reaction is conducted for about two hours to about 24 hours and preferably for 16 hours. The residue is dissolved in a solution of the hemicalcium salt of atorvastatin in dimethylformamide. The reaction mixture is heated at about 80° C. for about 22 hours.

Amlodipine may readily be prepared as described in U.S. Pat. No. 4,572,909 which is incorporated herein by reference. Amlodipine besylate, which is currently sold as Norvasc®, may be prepared as described in U.S. Pat. No. 4,879,303, which is incorporated herein by reference. Amlodipine and amlodipine besylate are potent and long lasting calcium channel blockers.

The R and S enantiomers of amlodipine may be prepared as described by Arrowsmith et al., J. Med. Chem., 1986, 29, 1696.

Atorvastatin may readily be prepared as described in U.S. Pat. No. 4,681,893, which is incorporated herein by reference. The hemicalcium salt of atorvastatin, which is currently sold as Lipitor®, may readily be prepared as described in U.S. Pat. No. 5,273,995, which is incorporated herein by reference.

The expression "pharmaceutically acceptable acid addition salts" is intended to define but is not limited to such salts as the hydrochloride, hydrobromide, sulfate, hydrogen sulfate, phosphate, hydrogen phosphate, dihydrogenphosphate, acetate, besylate, succinate, citrate, methanesulfonate (mesylate) and p-toluenesulfonate (tosylate) salts.

The acid addition salts of the instant prodrugs of amlodipine and atorvastatin may be readily prepared by reacting the free base form thereof with the appropriate acid. When the salt is of a monobasic acid (e.g., the hydrochloride, the hydrobromide, the p-toluenesulfonate, the acetate), the hydrogen form of a dibasic acid (e.g., the hydrogen sulfate, the succinate) or the dihydrogen form of a tribasic acid (e.g., the dihydrogen phosphate, the citrate), at least one molar equivalent and usually a molar excess of the acid is employed. However when such salts as the sulfate, the hemisuccinate, the hydrogen phosphate or the phosphate are desired, the appropriate and exact chemical equivalents of acid will generally be used. The free base and the acid are usually combined in a co-solvent from which the desired salt precipitates, or can be otherwise isolated by concentration and/or addition of a non-solvent.

In addition, the mutual prodrugs of amlodipine and atorvastatin of this invention and pharmaceutically acceptable salts thereof may occur as hydrates or solvates. Said hydrates and solvates are also within the scope of the invention.

The mutual prodrugs, pharmaceutical compositions and methods of this invention are all adapted to therapeutic use as agents in the treatment of atherosclerosis, angina pectoris, and a condition characterized by the presence of both hypertension and hyperlipidemia in mammals, particularly humans. Further, since these diseases and conditions are closely related to the development of cardiac disease and adverse cardiac conditions, these compounds, compositions and methods, by virtue of their action as antiatherosclerotics, antianginals, antihypertensives and antihyperlipidemics, are useful in the management of cardiac risk.

The utility of the compounds and compositions of the present invention as medical agents in the treatment of atherosclerosis in mammals (e.g. humans) is demonstrated by the activity of the compounds and compositions of this invention in conventional assays and the clinical protocol described below.

Effect of Mutual Prodrugs of Amlodipine and Atorvastatin on the Treatment of Atherosclerosis This study is a prospective randomized evaluation of the effect of a mutual prodrug of amlodipine and atorvastatin on the progression/regression of coronary and carotid artery disease. The study is used to show that a mutual prodrug of amlodipine and atorvastatin is effective in slowing or arresting the progression or causing regression of existing coronary artery disease (CAD) as evidenced by changes in coronary angiography or carotid ultrasound, in subjects with established disease.

This study is an angiographic documentation of coronary artery disease carried out as a double-blind, placebo-controlled trial of a minimum of about 500 subjects and preferably of about 780 to about 1200 subjects. It is especially preferred to study about 1200 subjects in this study. Subjects are admitted into the study after satisfying certain entry criteria set forth below.

Entry criteria: Subjects accepted for entry into this trial must satisfy certain criteria. Thus, the subject must be an adult, either male or female, aged 18–80 years of age in whom coronary angiography is clinically indicated. Subjects will have angiographic presence of a significant focal lesion such as 30% to 50% on subsequent evaluation by quantitative coronary angiography (QCA) in a minimum of one segment (non-PTCA, non-bypassed or non-MI vessel) that is judged not likely to require intervention over the next 3 years. It is required that the segments undergoing analysis have not been interfered with. Since percutaneous transluminal cardiac angioplasty (PTCA) interferes with segments by the insertion of a balloon catheter, non-PTCA segments are required for analysis. It is also required that the segments to be analyzed have not suffered a thrombotic event, such as a myocardial infarct (MI). Thus, the requirement for non-MI vessels. Segments that will be analyzed include: left main, proximal, mid and distal left anterior descending, first and second diagonal branch, proximal and distal left circumflex, first or largest space obtuse marginal, proximal, mid and distal right coronary artery. Subjects will have an ejection fraction of greater than 30% determined by catheterization or radionuclide ventriculography or ECHO cardiogram at the time of the qualifying angiogram or within the previous three months of the acceptance of the qualifying angiogram provided no intervening event such as a thrombotic event or procedure such as PTCA has occurred.

Generally, due to the number of patients and the physical limitations of any one facility, the study is carried out at multiple sites. At entry into the study, subjects undergo quantitative coronary angiography as well as B-mode carotid artery ultrasonography and assessment of carotid arterial compliance at designated testing centers. This establishes baselines for each subject. Once admitted into the test, subjects are randomized to receive amlodipine besylate (10 mgs) and placebo or atorvastatin calcium (10 mgs) and placebo or a mutual prodrug of amlodipine and atorvastatin or a pharmaceutically acceptable salt thereof (about 5 to 160 mgs). All doses set forth in this protocol are per day doses. The amount of amlodipine besylate may be varied as required. Generally, a subject will begin taking 10 mg and the amount will be titrated down to as little as 5 mg as determined by the clinical physician.

The subjects are monitored for a one to three year period, generally three years being preferred. B-mode carotid ultrasound assessment of carotid artery atherosclerosis and compliance are performed at regular intervals throughout the study. Generally, six month intervals are suitable. Typically this assessment is performed using B-mode ultrasound equipment. However, a person skilled in the art may use other methods of performing this assessment.

Coronary angiography is performed at the conclusion of the one to three year treatment period. The baseline and post-treatment angiograms and the intervening carotid artery B-mode ultrasonograms are evaluated for new lesions or progression of existing atherosclerotic lesions. Arterial compliance measurements are assessed for changes from baseline and over the 6-month evaluation periods.

The primary objective of this study is to show that the mutual prodrug of amlodipine and atorvastatin or pharmaceutically acceptable salts thereof reduces the progression of atherosclerotic lesions as measured by quantitative coronary angiography (QCA) in subjects with clinical coronary artery disease. QCA measures the opening in the lumen of the arteries measured.

The primary endpoint of the study is the change in the average mean segment diameter of the coronary artery tree. Thus, the diameter of an arterial segment is measured at various portions along the length of that segment. The average diameter of that segment is then determined. After the average segment diameter of many segments has been determined, the average of all segment averages is determined to arrive at the average mean segment diameter. The mean segment diameter of subjects taking the mutual prodrug of amlodipine and atorvastatin or pharmaceutically acceptable salts thereof will decline more slowly, will be halted completely, or there will be an increase in the mean segment diameter. These results represent slowed progression of atherosclerosis, halted progression of atherosclerosis and regression of atherosclerosis, respectively.

The secondary objective of this study is to show that the mutual prodrug of amlodipine and atorvastatin or a pharmaceutically acceptable salt thereof reduces the rate of progression of atherosclerosis in the carotid arteries as measured by the slope of the maximum intimal-medial thickness measurements averaged over 12 separate wall segments (Mean Max) as a function of time. The intimal-medial thickness of subjects taking the mutual prodrug of amlodipine and atorvastatin or a pharmaceutically acceptable salt thereof will increase more slowly, will cease to increase or will decrease. These results represent slowed progression of atherosclerosis, halted progression of atherosclerosis and regression of atherosclerosis, respectively.

The utility of the compounds and compositions of the present invention as medical agents in the treatment of angina pectoris in mammals (e.g., humans) is demonstrated by the activity of the compounds and compositions of this invention in conventional assays and the clinical protocol described below.

Effect of Mutual Prodrugs of Amlodipine and Atorvastatin on the Treatment of Angina This study is a double blind, parallel arm, randomized study to show the effectiveness of a mutual prodrug of amlodipine and atorvastatin or pharmaceutically acceptable salts thereof in the treatment of symptomatic angina.

Entry criteria: Subjects are males or females between 18 and 80 years of age with a history of typical chest pain associated with one of the following objective evidences of cardiac ischemia: (1) stress test segment elevation of about one millimeter or more from the ECG; (2) positive treadmill stress test; (3) new wall motion abnormality on ultrasound; or (4) coronary angiogram with a significant qualifying stenosis. Generally a stenosis of about 30–50% is considered to be significant.

Each subject is evaluated for about ten to thirty-two weeks. At least ten weeks are generally required to complete the study. Sufficient subjects are used in this screen to ensure that about 200 to 800 subjects and preferably about 400 subjects are evaluated to complete the study. Subjects are screened for compliance with the entry criteria, set forth above, during a four week run in phase. After the screening criteria are met, subjects are washed out from their current anti-anginal medication and stabilized on a long acting nitrate such as, for example, nitroglycerin, isosorbide-5-mononitrate or isosorbide dinitrate. The term "washed out", when used in connection with this screen, means the withdrawal of current anti-anginal medication so that substantially all of said medication is eliminated from the body of the subject. A period of eight weeks is preferably allowed for both the wash out period and for the establishment of the subject on stable doses of said nitrate. Subjects having one or two attacks of angina per week while on stable doses of long acting nitrate are generally permitted to skip the wash out phase. After subjects are stabilized on nitrates, the subjects enter the randomization phase provided the subjects continue to have either one or two angina attacks per week. In the randomization phase, the subjects are randomly placed into one of the four arms of the study set forth below. After completing the wash out phase, subjects in compliance with the entry criteria undergo twenty four hour ambulatory electrocardiogram (ECG) such as Holter monitoring, exercise stress testing such as a treadmill and evaluation of myocardial perfusion using PET (photon emission tomography) scanning to establish a baseline for each subject. When conducting a stress test, the speed of the treadmill and the gradient of the treadmill can be controlled by a technician. The speed of the treadmill and the angle of the gradient are generally increased during the test. The time intervals between each speed and gradient increase is generally determined using a modified Bruce Protocol.

After the baseline investigations have been completed, subjects are initiated on one of the following four arms of the study: (1) placebo; (2) atorvastatin calcium (about 2.5 mg to about 160 mg); (3) amlodipine besylate(about 2.5 mg to about 20 mg); or (4) a mutual prodrug of amlodipine and atorvastatin (about 5 to 160 mgs). The subjects are then monitored for two to twenty four weeks. It will be recognized by a person skilled in the art that a pharmaceutically acceptable salt of the mutual prodrug of amlodipine and atorvastatin may be used in the fourth arm of the study. Calculation of the dosage amount for these other forms of the mutual prodrug of amlodipine and atorvastatin is easily accomplished by performing a simple ratio relative to the molecular weights of the species involved.

After the monitoring period has ended, subjects will undergo the following investigations: (1) twenty four hour ambulatory ECG, such as Holter monitoring; (2) exercise stress testing (e.g. treadmill using said modified Bruce Protocol); and (3) evaluation of myocardial perfusion using PET scanning. Patients keep a diary of painful ischemic events and nitroglycerine consumption. It is generally desirable to have an accurate record of the number of anginal attacks suffered by the patient during the duration of the test. Since a patient generally takes nitroglycerin to ease the pain of an anginal attack, the number of times that the patient administers nitroglycerine provides a reasonably accurate record of the number of anginal attacks.

To demonstrate the effectiveness of the compounds and compositions of this invention, and to determine the dosage amounts of the mutual prodrug of this invention, the person conducting the test will evaluate the subject using the tests described. Successful treatment will yield fewer instances of ischemic events as detected by ECG, will allow the subject to exercise longer or at a higher intensity level on the treadmill, or to exercise without pain on the treadmill, or will yield better perfusion or fewer perfusion defects on photoemission tomography (PET).

The utility of the compounds and compositions of the present invention as medical agents in the treatment of hypertension and hyperlipidemia in mammals (e.g., humans) suffering from a combination of hypertension and hyperlipidemia is demonstrated by the activity of the compounds and compositions of this invention in conventional assays and the clinical protocol described below.

Effect of Mutual Prodrugs of Amlodipine and Atorvastatin on the Treatment of Subjects Having Both Hypertension and Hyperlipidemia This study is a double blind, parallel arm, randomized study to show the effectiveness of a mutual prodrug of amlodipine and atorvastatin or pharmaceutically acceptable salts thereof in controlling both hypertension and hyperlipidemia in subjects who have mild, moderate, or severe hypertension and hyperlipidemia.

Each subject is evaluated for 10 to 20 weeks and preferably for 14 weeks. Sufficient subjects are used in this screen to ensure that about 400 to 800 subjects are evaluated to complete the study.

Entry criteria: Subjects are male or female adults between 18 and 80 years of age having both hyperlipidemia and hypertension. The presence of hyperlipidemia is evidenced by evaluation of the low density lipoprotein (LDL) level of the subject relative to certain positive risk factors. If the subject has no coronary heart disease (CHD) and has less than two positive risk factors, then the subject is considered to have hyperlipidemia if the LDL of the subject is greater than or equal to 190. If the subject has no CHD and has two or more positive risk factors, then the subject is considered to have hyperlipidemia if the LDL of the subject is greater than or equal to 160. If the subject has CHD, then the subject is considered to have hyperlipidemia if the LDL of the subject is greater than or equal to 130.

Positive risk factors include (1) male over 45, (2) female over 55 wherein said female is not undergoing hormone replacement therapy (HRT), (3) family history of premature cardiovascular disease, (4) the subject is a current smoker, (5) the subject has diabetes, (6) an HDL of less than 45, and (7) the subject has hypertension. An HDL of greater than 60 is considered a negative risk factor and will offset one of the above mentioned positive risk factors.

The presence of hypertension is evidenced by a sitting diastolic blood pressure (BP) of greater than 90 or sitting systolic BP of greater than 140. All blood pressures are generally determined as the average of three measurements taken five minutes apart.

Subjects are screened for compliance with the entry criteria set forth above. After all screening criteria are met, subjects are washed out from their current antihypertensive and lipid lowering medication and are placed on the NCEP ATP II Step 1 diet. The NCEP ATP II (adult treatment panel, 2nd revision) Step 1 diet sets forth the amount of saturated and unsaturated fat which can be consumed as a proportion of the total caloric intake. The term "washed out" where used in connection with this protocol, means the withdrawal of current antihypertensive and lipid lowering medication so that substantially all of said medication is eliminated from the body of the subject. Newly diagnosed subjects generally remain untreated until the test begins. These subjects are also placed on the NCEP Step 1 diet. After the four week wash out and diet stabilization period, subjects undergo the following baseline investigations: (1) blood pressure and (2) fasting lipid screen. The fasting lipid screen determines baseline lipid levels in the fasting state of a subject. Generally, the subject abstains from food for twelve hours, at which time lipid levels are measured.

After the baseline investigations are performed subjects are started on one of the following: (1) a fixed dose of amlodipine besylate, generally about 2.5 to 10 mg; (2) a fixed dose of atorvastatin calcium, generally about 10 to 80 mg; or (3) a mutual prodrug of amlodipine and atorvastatin (about 5 to 160 mgs). Subjects remain on these doses for a minimum of six weeks, and generally for no more than eight weeks. It will be recognized by a skilled person that a pharmaceutically acceptable salt of the mutual prodrug of amlodipine and atorvastatin may be used in the third arm of this investigation. Calculation of the dosage amount for these forms of the mutual prodrug of amlodipine and atorvastatin is easily accomplished by performing a simple ratio relative to the molecular weights of the species involved. The subjects return to the testing center at the conclusion of the six to eight weeks so that the baseline evaluations can be repeated. The blood pressure of the subject at the conclusion of the study is compared with the blood pressure of the subject upon entry. The lipid screen measures the total cholesterol, LDL-cholesterol, HDL-cholesterol, triglycerides, apoB, VLDL (very low density lipoprotein) and other components of the lipid profile of the subject. Improvements in the values obtained after treatment relative to pretreatment values indicate the utility of the test compound.

The utility of the compounds and compositions of the present invention as medical agents in the management of cardiac risk in mammals (e.g., humans) at risk for an adverse cardiac event is demonstrated by the activity of the compounds and compositions of this invention in conventional assays and the clinical protocol described below.

Effects of Mutual Prodrugs of Amlodipine and Atorvastatin on Subjects at Risk of Future Cardiovascular Events This study is a double blind, parallel arm, randomized study to show the effectiveness of a mutual prodrug of amlodipine and atorvastatin or pharmaceutically acceptable salts thereof in reducing the overall calculated risk of future events in subjects who are at risk for having future cardiovascular events. This risk is calculated by using the Framingham Risk Equation. A subject is considered to be at risk of having a future cardiovascular event if that subject is more than one standard deviation above the mean as calculated by the Framingham Risk Equation. The study is used to evaluate the efficacy of a mutual prodrug of amlodipine and atorvastatin in controlling cardiovascular risk by controlling both hypertension and hyperlipidemia in patients who have both mild to moderate hypertension and hyperlipidemia.

Each subject is evaluated for 10 to 20 weeks and preferably for 14 weeks. Sufficient subjects are recruited to ensure that about 400 to 800 subjects are evaluated to complete the study.

Entry criteria: Subjects included in the study are male or female adult subjects between 18 and 80 years of age with a baseline five year risk which risk is above the median for said subject's age and sex, as defined by the Framingham Heart Study, which is an ongoing prospective study of adult men and women showing that certain risk factors can be used to predict the development of coronary heart disease. The age, sex, systolic and diastolic blood pressure, smoking habit, presence or absence of carbohydrate intolerance, presence or absence of left ventricular hypertrophy, serum cholesterol and high density lipoprotein (HDL) of more than one standard deviation above the norm for the Framingham Population are all evaluated in determining whether a patient is at risk for adverse cardiac event. The values for the risk factors are inserted into the Framingham Risk equation and calculated to determine whether a subject is at risk for a future cardiovascular event.

Subjects are screened for compliance with the entry criteria set forth above. After all screening criteria are met, patients are washed out from their current antihypertensive and lipid lowering medication and any other medication which will impact the results of the screen. The patients are then placed on the NCEP ATP II Step 1 diet, as described in the hypertension and hyperlipidemia section above. Newly diagnosed subjects generally remain untreated until the test begins. These subjects are also placed on the NCEP ATP II Step 1 diet. After the four week wash out and diet stabilization period, subjects undergo the following baseline investigations: (1) blood pressure; (2) fasting; (3) lipid screen; (4) glucose tolerance test; (5) ECG; and (6) cardiac ultrasound. These tests are carried out using standard procedures well known to persons skilled in the art. The ECG and the cardiac ultrasound are generally used to measure the presence or absence of left ventricular hypertrophy.

After the baseline investigations are performed patients will be started on one of the following: (1) a fixed dose of amlodipine (about 2.5 to 10 mg); (2) a fixed dose of atorvastatin (about 10 to 80 mg); or (3) a mutual prodrug of amlodipine and atorvastatin (about 5 to 160 mgs). It will be recognized by a skilled person that a pharmaceutically acceptable salt of a mutual prodrug of amlodipine and atorvastatin may be used in this invention. Calculation of the dosage amount for these other forms of a mutual prodrug of amlodipine and atorvastatin is easily accomplished by performing a simple ratio relative to the molecular weights of the species involved. Patients are kept on these doses and are asked to return in six to eight weeks so that the baseline evaluations can be repeated. At this time the new values are entered into the Framingham Risk equation to determine whether the subject has a lower, greater or no change in the risk of future cardiovascular event.

The above assays demonstrating the effectiveness of a mutual prodrug of amlodipine and atorvastatin or pharmaceutically acceptable salts thereof in the treatment of angina pectoris, atherosclerosis, hypertension and hyperlipidemia together, and the management of cardiac risk, also provide a means whereby the activities of the compounds of this invention can be compared between themselves and with the activities of other known compounds. The results of these comparisons are useful for determining dosage levels in mammals, including humans, for the treatment of such diseases.

The following dosage amounts and other dosage amounts set forth elsewhere in the specification and in the appendant claims are for an average human subject having a weight of about 65 kg to about 70 kg. The skilled practitioner will readily be able to determine the dosage amount required for a subject whose weight falls outside the 65 kg to 70 kg range, based upon the medical history of the subject and the presence of diseases, e.g., diabetes, in the subject. All doses set forth herein, and in the appendant claims, are daily doses.

In general, in accordance with this invention, a mutual prodrug of amlodipine and atorvastatin is generally administered in a dosage of about 2.5 mg to about 20 mg. It will be recognized by a skilled person that the free base form or other salt forms of the mutual prodrug of amlodipine and atorvastatin may be used in this invention. Calculation of the dosage amount for these other forms of the mutual prodrug of amlodipine and atorvastatin is easily accomplished by performing a simple ratio relative to the molecular weights of the species involved.

The compounds of the present invention are generally administered in the form of a pharmaceutical composition comprising a compound of this invention together with a pharmaceutically acceptable carrier, vehicle or diluent. Thus, the compounds of this invention can be administered either individually or together in any conventional oral, parenteral or transdermal dosage form.

For oral administration a pharmaceutical composition can take the form of solutions, suspensions, tablets, pills, capsules, powders, and the like. Tablets containing various excipients such as sodium citrate, calcium carbonate and calcium phosphate are employed along with various disintegrants such as starch and preferably potato or tapioca starch and certain complex silicates, together with binding agents such as polyvinylpyrrolidone, sucrose, gelatin and acacia. Additionally, lubricating agents such as magnesium stearate, sodium lauryl sulfate and talc are often very useful for tabletting purposes. Solid compositions of a similar type are also employed as fillers in soft and hard-filled gelatin capsules; preferred materials in this connection also include lactose or milk sugar as well as high molecular weight polyethylene glycols. When aqueous suspensions and/or elixirs are desired for oral administration, the compounds of this invention can be combined with various sweetening agents, flavoring agents, coloring agents, emulsifying agents and/or suspending agents, as well as such diluents as water, ethanol, propylene glycol, glycerin and various like combinations thereof.

The compositions of this invention may also be administered in a controlled release formulation such as a slow release or a fast release formulation. Such controlled release dosage formulations of the compounds of this invention may be prepared using methods well known to those skilled in the art. The method of preferred administration will be determined by the attendant physician or other person skilled in the art after an evaluation of the subject's condition and requirements.

For purposes of parenteral administration, solutions in sesame or peanut oil or in aqueous propylene glycol can be employed, as well as sterile aqueous solutions of the corresponding water-soluble salts. Such aqueous solutions may be suitably buffered, if necessary, and the liquid diluent first rendered isotonic with sufficient saline or glucose. These aqueous solutions are especially suitable for intravenous, intramuscular, subcutaneous and intraperitoneal injection purposes. In this connection, the sterile aqueous media employed are all readily obtainable by standard techniques well-known to those skilled in the art.

Methods of preparing various pharmaceutical compositions with a certain amount of active ingredient are known, or will be apparent in light of this disclosure, to those skilled in this art. For examples, see *Remington's Pharmaceutical Sciences,* Mack Publishing Company, Easton, Pa., 19*th* Edition (1995).

Pharmaceutical compositions according to the invention may contain 0.1%–95% of the compound(s) of this invention, preferably 1%–70%. In any event, the composition to be administered will contain a quantity of a compound(s) according to the invention in an amount effective to treat the condition or disease of the subject being treated.

It should be understood that the invention is not limited to the particular embodiments described herein, but that various changes and modifications may be made without departing from the spirit and scope of this novel concept as defined by the following claims.

EXAMPLE ONE 4-(2-Chloro-phenyl)-2-(2-[(5-{7-[2-(4-fluoro-phenyl)-5-isopropyl-3-phenyl-4-phenylcarbamoyl-pyrrol-1-yl]-3,5-dihydroxy-heptanoyloxymethyl}-2-oxo-[1,3]dioxol-4-ylmethyl)-amino]-ethoxymethyl}-6-methyl-1,4-dihydro-pyridine-3,5-dicarboxylic acid 3-ethylester 5-methyl ester A solution of 4,5-bis(bromomethyl)-1,3-dioxol-2-one (10 g, 36.8 mmol) in ethyl acetate (10 ml) is added dropwise to a mixture of atorvastatin (7.45 g, 12.9 mmol), potassium bicarbonate (3 g) and sodium iodide (0.05 g) in ethyl acetate (60 ml) and N,N-dimethylformamide (20 ml) at 5° C. and the mixture is stirred at room temperature for 8 h. Cold water (30 ml) is added with stirring and the organic phase is separated, washed with 5% aqueous sodium chloride and dried over anhydrous sodium sulfate. The solvent is removed under reduced pressure and the residue is purified by column chromatography on silica gel to yield the 5-bromomethyl-2-oxo-1,3-dioxol-4-yl)methyl ester of atorvastatin. A mixture of the 5-bromomethyl-2-oxo-1,3-dioxol-4-yl)methyl ester of atorvastatin (7.7 g, 10 mmol), amlodipine (5.25 g, 10 mmol) and potassium bicarbonate (1 g, 10 mmol) in N,N-dimethylformamide (50 ml) is stirred at 0° C. for 8 h. The solvent is removed in vacuo and the residue is dissolved in chloroform. The chloroform solution is washed with water, dried over anhydrous sodium sulfate and concentrated under reduced pressure to yield the title compound of Example One.

EXAMPLE TWO

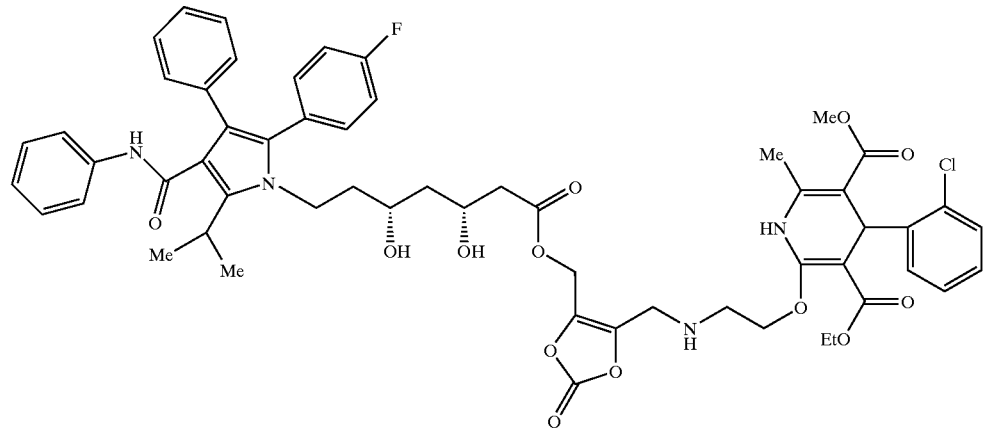

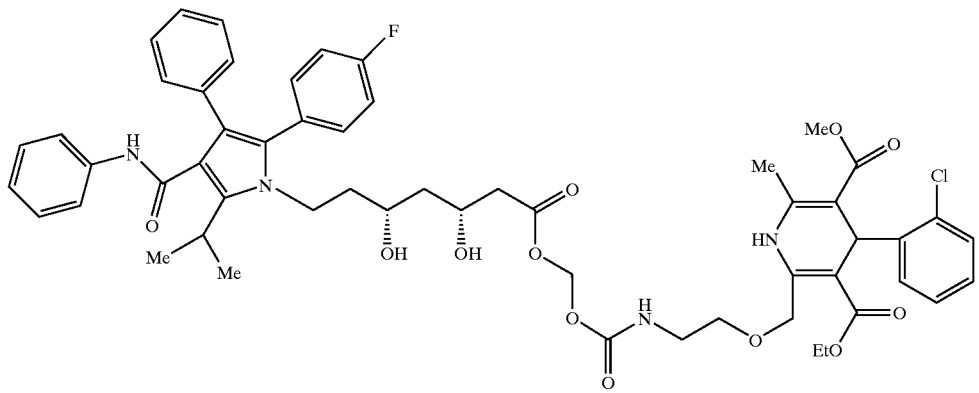

4-(2-Chloro-phenyl)-2-(2-{7-[2-(4-fluoro-phenyl)-5-isopropyl-3-phenyl-4-phenylcarbamoyl-pyrrol-1-yl]-3,5-dihydroxy-heptanoyloxymethoxycarbonylamino}-ethoxymethyl)-6-methyl-1,4-dihydro-pyridine-3,5-dicarboxylic acid 3-ethyl ester 5-methyl ester Chloromethyl chloroformate (2.85 g, 22 mmol) is added to amlodipine (10.5 g, 20 mmol) and pyridine (1.6 g) in 300 ml chloroform cooled in an ice bath. The reaction mixture is stirred at room temperature for 16 h, washed with water, dried (anhydrous sodium sulfate) and concentrated under reduced pressure. The residue is dissolved in dimethylformamide (50 ml) containing the calcium salt of atorvastatin (10.75 g, 0.018 mol) and the reaction mixture is heated at 80° C. for 20 h. The dimethylformamide is removed in vacuo and the residue is triturated with chloroform-hexane to yield the title compound the title compound of Example Two.

What is claimed is:

1. A compound which is a mutual prodrug of amlodipine and atorvastatin or a pharmaceutically acceptable salt thereof.

2. A compound of claim 1 having the formula I,

3. A compound of claim 2 or pharmaceutically acceptable salt thereof wherein the carbon atom at the 4-position of the dihydropyridine ring has the (R)-configuration.

4. A compound of claim 2 or pharmaceutically acceptable salt thereof wherein the carbon atom at the 4-position of the dihydropyridine ring has the (S)-configuration.

5. A compound of claim 1 having the formula II,

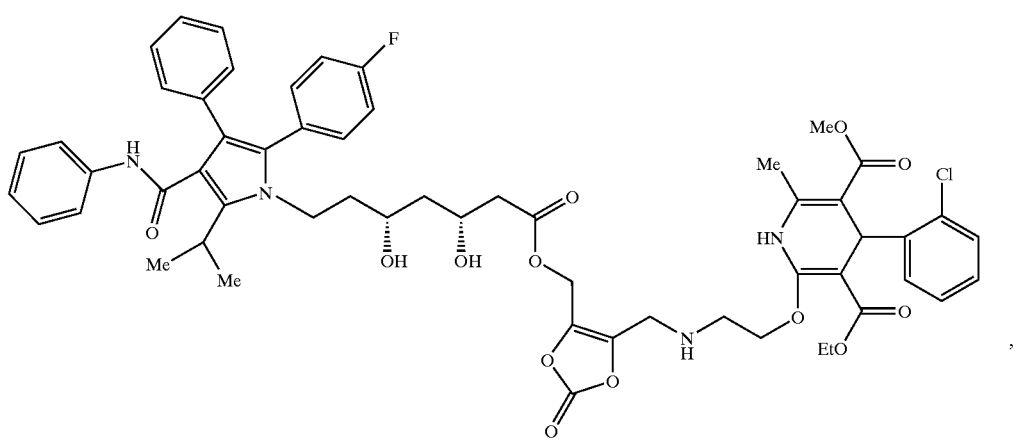

or a pharmaceutically acceptable salt thereof.

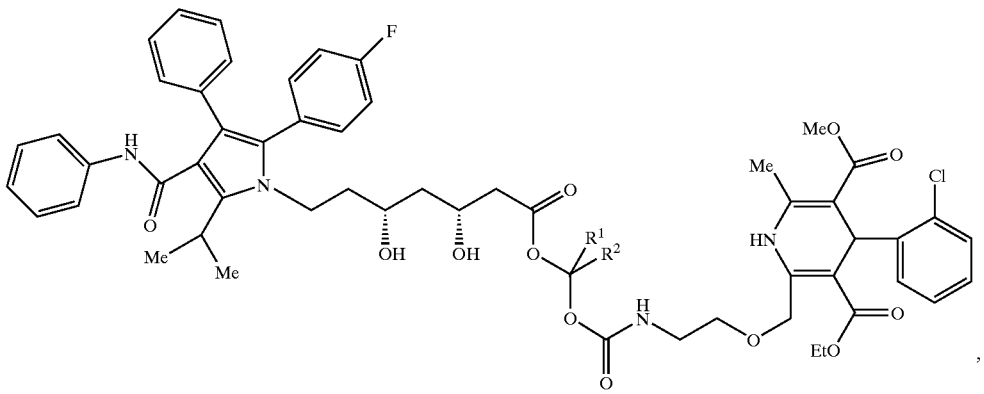

or a pharmaceutically acceptable salt thereof,
wherein $R^1$ and $R^2$ are independently selected from H and $(C_1-C_4)$alkyl.

6. A compound of claim 5 or a pharmaceutically acceptable salt thereof wherein $R^1$ and $R^2$ are each H.

7. A compound of claim 6 or a pharmaceutically acceptable salt thereof wherein the carbon atom at the 4-position of the dihydropyridine ring has the (R)-configuration.

8. A compound of claim 6 or a pharmaceutically acceptable salt thereof wherein the carbon atom at the 4-position of the dihydropyridine ring has the (S)-configuration.

9. 4-(2-Chloro-phenyl)-2-(2-[(5-{7-[2-(4-fluoro-phenyl)-5-isopropyl-3-phenyl-4-phenylcarbamoyl-pyrrol-1-yl]-3,5-dihydroxy-heptanoyloxymethyl}-2-oxo-[1,3]dioxol-4-ylmethyl)-amino]-ethoxymethyl}-6-methyl-1,4-dihydro-pyridine-3,5-dicarboxylic acid 3-ethylester 5-methyl ester.

10. 4-(2-Chloro-phenyl)-2-(2-{7-[2-(4-fluoro-phenyl)-5-isopropyl-3-phenyl-4-phenylcarbamoyl-pyrrol-1-yl]-3,5-dihydroxy-heptanoyloxymethoxycarbonylamino}-ethoxymethyl)-6-methyl-1,4-dihydro-pyridine-3,5-dicarboxylic acid 3-ethyl ester 5-methyl ester.

11. A pharmaceutical composition comprising a compound of claim 1 and a pharmaceutically acceptable carrier, vehicle or diluent.

12. A composition of claim 11 wherein said compound of claim 1 is 4-(2-chloro-phenyl)-2-(2-[(5-{7-[2-(4-fluoro-phenyl)-5-isopropyl-3-phenyl-4-phenylcarbamoyl-pyrrol-1-yl]-3,5-dihydroxy-heptanoyloxymethyl}-2-oxo-[1,3]dioxol-4-ylmethyl)-amino]-ethoxymethyl}-6-methyl-1,4-dihydro-pyridine-3,5-dicarboxylic acid 3-ethylester 5-methyl ester.

13. A composition of claim 11 wherein said compound of claim 1 is 4-(2-chloro-phenyl)-2-(2-{7-[2-(4-fluoro-phenyl)-5-isopropyl-3-phenyl-4-phenylcarbamoyl-pyrrol-1-yl]-3,5-dihydroxy-heptanoyloxymethoxycarbonylamino}-ethoxymethyl)-6-methyl-1,4-dihydro-pyridine-3,5-dicarboxylic acid 3-ethyl ester 5-methyl ester.

14. A method of treating angina pectoris in a mammal suffering from angina pectoris comprising administering to said mammal an angina pectoris treating effective amount of a compound of claim 1 or a pharmaceutically acceptable salt thereof.

15. A method of treating a mammal suffering from angina pectoris comprising administering to said mammal an angina pectoris treating effective amount of a pharmaceutical composition of claim 11.

16. A method of treating hypertension and hyperlipidemia in a mammal suffering from hypertension and hyperlipidemia comprising administering to said mammal a hypertension and hyperlipidemia treating effective amount of a compound of claim 1 or a pharmaceutically acceptable salt thereof.

17. A method of treating hypertension and hyperlipidemia in a mammal suffering from hypertension and hyperlipidemia comprising administering to said mammal a hypertension and hyperlipidemia treating effective amount of a pharmaceutical composition of claim 11.

18. A method of treating atherosclerosis in a mammal suffering from atherosclerosis comprising administering to said mammal an antiatherosclerosis effective amount of a compound of claim 1 or a pharmaceutically acceptable salt thereof.

19. A method of claim 18 wherein progression of atherosclerotic plaques is slowed.

20. A method of claim 19 wherein said progression of atherosclerotic plaques is slowed in coronary arteries.

21. A method of claim 19 wherein said progression of atherosclerotic plaques is slowed in carotid arteries.

22. A method of claim 19 wherein said progression of atherosclerotic plaques is slowed in the peripheral arterial system.

23. A method of claim 18 wherein regression of atherosclerotic plaques occurs.

24. A method of claim 23 wherein said regression of atherosclerotic plaques occurs in coronary arteries.

25. A method of claim 23 wherein said regression of atherosclerotic plaques occurs in carotid arteries.

26. A method of claim 23 wherein said regression of atherosclerotic plaques occurs in the peripheral arterial system.

27. A method of treating atherosclerosis in a mammal suffering from atherosclerosis comprising administering to said mammal an antiatherosclerosis effective amount of a pharmaceutical composition of claim 11.

28. A method of managing cardiac risk in a mammal at risk of suffering an adverse cardiac event, comprising administering to said mammal a cardiac risk treating effective amount of a compound of claim 1 or a pharmaceutically acceptable salt thereof.

29. A method of managing cardiac risk in a mammal at risk of suffering an adverse cardiac event, comprising administering to said mammal a cardiac risk treating effective amount of a pharmaceutical composition of claim 11.

30. A method of preparing atorvastatin in vivo comprising administering to a mammal a compound of claim 1 or a pharmaceutically acceptable salt thereof.

31. A method of claim 30 wherein said mammal is a human.

32. A method of preparing amlodipine in vivo comprising administering to a mammal a compound of claim 1 or a pharmaceutically acceptable salt thereof.

33. A method of claim 32 wherein said mammal is a human.

34. A method of treating a mammal with amlodipine comprising administering to said mammal a compound of claim 1 or a pharmaceutically acceptable salt thereof.

35. A method of treating a mammal with atorvastatin comprising administering to said mammal a compound of claim 1 or a pharmaceutically acceptable salt thereof.

36. A pharmaceutical composition comprising an amount of a compound of claim 1 or a pharmaceutically acceptable salt thereof and an amount of amlodipine or a pharmaceutically acceptable salt thereof.

37. A composition of claim 36 comprising the besylate salt of amlodipine.

38. A pharmaceutical composition comprising an amount of a compound of claim 1 or a pharmaceutically acceptable salt thereof and an amount of atorvastatin or a pharmaceutically acceptable salt thereof.

39. A composition of claim 38 comprising the hemicalcium salt of atorvastatin.

40. A method of treating angina pectoris in a mammal suffering from angina pectoris comprising administering to said mammal an effective amount of a pharmaceutical composition of claim 36.

41. A method of treating angina pectoris in a mammal suffering form angina pectoris comprising administering to said mammal an effective amount of a pharmaceutical composition of claim 38.

42. A method of treating atherosclerosis in a mammal comprising administering to said mammal an atherosclerosis treating effective amount of a pharmaceutical composition of claim 36.

43. A method of treating atherosclerosis in a mammal comprising administering to said mammal an atherosclerosis treating effective amount of a pharmaceutical composition of claim 38.

44. A method of managing cardiac risk in a mammal comprising administering to said mammal a cardiac risk treating effective amount of a pharmaceutical composition of claim 36.

45. A method of managing cardiac risk in a mammal comprising administering to said mammal a cardiac risk treating effective amount of a pharmaceutical composition of claim 38.

46. A method of treating a mammal suffering from hypertension and hyperlipidemia comprising administering to said mammal a hypertension and hyperlipidemia treating effective amount of a pharmaceutical composition of claim 36.

47. A method of treating a mammal suffering from hypertension and hyperlipidemia comprising administering to said mammal a hypertension and hyperlipidemia treating effective amount of a pharmaceutical composition of claim 38.

* * * * *